United States Patent [19]

Wellinghoff

[11] Patent Number: 5,939,356
[45] Date of Patent: Aug. 17, 1999

[54] CONTROLLED RELEASE COATED AGRICULTURAL PRODUCTS

[75] Inventor: Stephen T. Wellinghoff, San Antonio, Tex.

[73] Assignee: Southwest Research Institute, San Antonio, Tex.

[21] Appl. No.: 08/878,667

[22] Filed: Jun. 19, 1997

Related U.S. Application Data

[60] Provisional application No. 60/020,790, Jun. 21, 1996.
[51] Int. Cl.$^6$ ..................................................... A01N 25/26
[52] U.S. Cl. ............................................ 504/100; 504/116
[58] Field of Search ............................. 425/405; 504/116, 504/100; 514/951, 962; 424/490, 497

[56] References Cited

U.S. PATENT DOCUMENTS

| | | | |
|---|---|---|---|
| 4,290,816 | 9/1981 | Ludwig et al. | 106/287 |
| 4,507,142 | 3/1985 | Pace et al. | 71/83 |
| 5,223,525 | 6/1993 | Wu et al. | 514/398 |
| 5,356,467 | 10/1994 | Oshlack et al. | 106/153 |
| 5,472,712 | 12/1995 | Oshlack et al. | 424/480 |

*Primary Examiner*—Jose' G. Dees
*Assistant Examiner*—Alton Pryor
*Attorney, Agent, or Firm*—John L. Sigalos

[57] ABSTRACT

Controlled release coated agricultural products comprising agricultural chemicals, seed, or mixtures thereof coated with an environmentally degradable amorphous alkene-sulfur copolymer are disclosed. Also disclosed is the process of making such products, preferably by coating with a molten copolymer and then cooling to harden the coating of copolymer about the agricultural products.

20 Claims, No Drawings

CONTROLLED RELEASE COATED AGRICULTURAL PRODUCTS

CROSS-REFERENCE TO RELATED APPLICATIONS

This application claims the benefit of prior filed co-pending U.S. Provisional Application No. 60/020,790, filed Jun. 21, 1996.

BACKGROUND OF THE INVENTION

The present invention relates to controlled release coated agricultural products, particularly agricultural chemicals and seeds, and to the process of making the same.

It is known to coat agricultural chemicals ("agrichemicals"), such a fertilizers, soil conditioners, fungicides, insecticides, herbicides, nematocides, plant hormones, insect repellents, and the like, in order to control their release over varying periods of time after they have been applied. The purpose is to permit controlled release thereof over an extended period of time and thereby ensure that the beneficial effects are maximized, or to delay the release thereof until such time as it is desired that the beneficial effects be used.

The coatings that have been used for these have varied, some of them being released by environmental dissolution factors, such as the air, oxygen, or water, and some by microbial degradation, and some by a combination of all. Toward this end, these have include a variety of polymers and other materials such as waxes and the like. To date, however, none of such coatings has been satisfactory for a variety of reasons. Thus, for example, it has been known to coat agrichemicals, such as urea, with sulfur in which the semi-crystalline sulfur coats the urea, provides small channels for the entrance of water, and the subsequent extraction of urea. Polymer or wax coatings are applied to seal the small channel or cracks and the sulfur layer to obtain a longer term or a delayed release. The operative mechanism for release is diffusion control through the microcrack sealed polymer. However, it is difficult to control the rate of release due to the difficulty in controlling the number and sizing of the microcracks and the amount of polymer or wax as needed to seal the same in order to get the desired release schedule. In agricultural usage, it is important that the release be predictable in order that the agrichemical be released at the proper time in the growth cycle of the particular crop to which it has been applied. If, for example, a pesticide is to be applied, but it is not released until after the time at which the attacking pest is due to act on the plant it, of course, becomes essentially a worthless product.

With respect to seeds, certain of them, such as corn, are especially susceptible to premature swelling by water-laden soils, which can prevent their proper germination. It has long been desired to protect such seeds from such excess water with a hydrophobic coating which would be capable of biodegrading at a known rate. This would enable the seed to be sown at a desirable time or even under adverse conditions, and through bacterial erosion of the coating have the seed available for germination under less adverse conditions. Such coatings previously used, however, have a number of drawbacks, some of which require the use of solvents, which are often deleterious to the seed. In addition, as previously noted, certain of them, such as sulfur coatings, tend to have microcracks and, as such, difficult to properly coat them to get the desired release rates.

There are also coating procedures which utilize materials which are costly and make them uneconomic and often the coating materials themselves are deleterious to the environment. This is particularly true with certain of the polymers which utilize formaldehyde, which can adversely affect the soil.

SUMMARY OF THE INVENTION

The present invention overcomes the problems of the prior art and provides controlled release agricultural products and a process for forming the same which is economical, which products leave behind environmentally acceptable and friendly by-products, and which are solvent-free.

Briefly stated, the present invention comprises compositions comprising a controlled release coated agricultural product comprising an agricultural chemical and/or seed coated with a layer of an amorphous alkene-sulfur copolymer. Such coatings are environmentally degradable.

The present invention also provides the process for making such agricultural products comprising encapsulating an agricultural chemical, seed, or mixture thereof with a coating of an environmentally degradable amorphous alkene-sulfur copolymer, with the thickness of the coating being sufficient to control release of the encapsulated agricultural chemical and/or seed at a desired rate. The layer can be hardened by air or liquid cooling.

DETAILED DESCRIPTION

As used herein, the term "agricultural product" means any agrichemical, seed, or other agricultural item, that has been coated in order to control its release or germination.

With respect to the term "agrichemical", this means any chemical compound or mixture used to increase the productivity and quality of or protect farm crops, and includes fertilizers, soil conditioners, fungicides, insecticides, herbicides, nematocides, plant harmones, insect repellents, and the like, and mixtures thereof. It is, of course, known to incorporate with coated seeds a fertilizer therefor and/or other chemicals such as herbicides, insecticides, and the like.

As to the seeds that can be utilized, corn is a prime example with soybeans and sunflower seeds being other illustrative examples.

In describing the instant invention, reference will be had to urea capsules as the agrichemical, and corn as the seed, it being understood that they are merely exemplary of the agrichemicals and seeds that can be used.

An essential aspect of the instant invention is the utilization of amorphous alkene-sulfur copolymers containing dissolved $S_8$ and polymeric sulfur. Such copolymers are the subject of U.S. Pat. No. 4,290,816, the entirety of the disclosure of such patent being specifically incorporated herein by reference. Such patent describes the preparation of sulfur polymers by reacting sulfur with a mixture of alkenes to stabilize the amorphous state of the sulfur indefinitely.

According to Bordoloi and Pearce [B. K. Bordoloi and E. M. Pearce, Advances in Chemistry Series, 165, 31, 1977] complete stabilization of the sulfur in the amorphous regions of the polymer as $S_8$ requires substantial reaction into the alkene copolymer (dicyclopentadiene) which must be added to the sulfur at 32–50 mole % (20–34 wt. %). Otherwise substantial conversion of polymeric sulfur to $S_8$ and subsequent crystallization to large embrittling, orthorhombic crystals of $S_8$ will occur. A typical alloy made by reacting 25 wt. % dicyclopentadiene and 75 wt. % sulfur at 140° C. for 3 hours will contain 54.7% of the sulfur as copolymer, 17% as monoclinic sulfur monomer and 28.3% amorphous $S_8$ after aging 18 hours at room temperature. Increasing the reaction time to 20 hours completely eliminates even monoclinic sulfur and yields 68.7% of sulfur as copolymer and 31.3% as amorphous $S_8$ [Bordoloi and Pearce, ibid. p. 13].

The principal advantage of the invention disclosed in U.S. Pat. No. 4,290,816 is that the specific mixtures of alkenes enables the polymerization of $S_8$ and incorporation into an alkene sulfur copolymer to occur in a controlled fashion, preventing runaway viscosity increases typical of other processes such as reaction of sulfur and dicyclopentadiene. In addition, upon cooling to room temperature, monomeric sulfur will not crystallize from these rubbery or glassy mixtures. It remains dissolved in the amorphous regions as a plasticizer to prevent embrittlement and cracking of the material. Normally, the semicrystalline amorphous sulfur that is produced consists of partially crystalline polymeric sulfur with the amorphous regions plasticized by $S_8$ monomer so that the $T_g$ is below room temperature. However, over time, the $S_8$ will crystallize, causing the $T_g$ to approach 75° C. and thus removing the plasticizing effect at room temperature.

More specifically, sulfur (<50 mole %) is reacted with a first diolefin such as dicyclopentadiene or its mixtures with dimer, trimer, and tetramer (10–35 mole %) and a second monoolefin such as vinyl toluene or pinene or an industrial mixture of mono and diolefin, such as dipentene, which contains a large percentage of monoolefin (10–35 mole %). Normally, reaction of sulfur with the diolefin produces very high molecular weight or gel while reaction with monoolefin produces low molecular weight materials which do not retard sulfur crystallization. Reactions of -sulfur with the mixtures of the two most probably terminates the polymerization at an ideal inter-mediate molecular weight that can still retard sulfur crystallization.

Once the alkene-sulfir-amorphous sulfur alloy has been produced, it is necessary to reduce the viscosity of the material to <400 cP for coating by spray drying and Wurster air suspension coating or the <2000 cP for disk coating at the coating temperature which is preferably between 50–80° C. for seeds and 50–135° C. for urea particles or urea-salt eutectics containing the agriculturally active ingredients. In addition, the coating must cool to a hard, leathery consistency upon cooling to room temperature.

One of the most effective methods to accomplish this is by diluting the reaction mixture with an alkyl polysulfide plasticizer, $R(S)_nR$, where n=4,5 and R is a long chain alkyl $C_mH_{2m+1}$ where m=10–16 [see Bordoloi and Pearce]. Typical mixtures would contain 70–50 wt. % sulfur, 30–40% wt. % alkene and 10–20% wt. % polysulfide plasticizer. Other conventional plasticizers suitable for this purpose can be utilized.

As is known, depending upon the particular release rate desired, one can vary the thickness of the shell or capsule about the urea or the seed. This is dictated by the thickness and particular polymer coating, but ordinarily capsules with a wall thickness of about 2 to 20 microns, are preferred for both chemical and seed use. The thickness of any particular alkene-sulfur copolymer to give the release rate desired can be determined by routine experimentation since, as described below, such polymers have a known rate of microbial degradation.

The shell is hardened by simply utilizing a conventional air quench using a temperature be-low the glass transition temperature of the shell material. Ordinarily the alkene-sulfur copolymer, sulfur, plasticizer systems have a glass transition temperature in the range of about 50 to 70° C. moreover, their usual melt temperatures are 50 to 140° C. Since the encapsulation time is very brief, such melt temperature permits encapsulation of the urea of the chemicals and the seeds without any damage thereto. Corn, for example, can be exposed to temperatures in excess of 120° C. for several seconds without any deleterious effect and the instant encapsulation procedure is substantially well completed before such time.

A large advantage of the instant process is that the polymers are solvent-free and melted to be encapsulated without the need for any solvent. Moreover, because of their amorphous nature, they are microcrack-free and do not require the utilization of any oily or waxy layer in order to seal any microcracks.

As noted, the thickness of any particular copolymer shell is regulated by the particular release rate required. The alkene-sulfur, sulfur, plasticizer systems are susceptible to microbial degradation by known soil oxidizing bacteria, such as *Thiobacillus thiooxidans*. These require only sulfur and organics available in the soil as a food source and these are readily available in agricultural soil environments. There are also certain heterotrophic organisms which can also degrade the polymers. It has been noted that bacterial erosion of the sulfur capsule about the core urea or seed, such as corn, is quite uniform and has an average rate of oxidation such that typical soil bacteria can oxidize about 1 micron of a layer in 43 days at about 30° C. and ambient moisture conditions. The rate of oxidation is maximized at moisture contents close to field capacity, except in certain sand and clay-based soils where water fills desirable air pores in such soils. Thus, by varying the micron size of the shell, one can adjust the rate at which the shell or capsule material will be degraded to release the core agrichemical or seed.

It will also be evident that if one is desirous of applying an agrichemical, such as a fertilizer, over a long period of time, one can coat various batches of the urea with different thickness coatings of the alkene-sulfur copolymer and then admix the various coated ureas. The result will be that those with the submicron coatings will be releasing the urea possibly within a weeks, while those having the larger micron-size coatings will release the urea over periods extending for periods of months.

It is also an aspect of the present invention that certain of the agrichemicals can be admixed with the molten polymer as it is placed about the seed to encapsulate the same. This will enable a fertilizer, for example, to be placed into the ground, for example, prior to the seed being exposed, or if desired, it is possible to add a pesticide within the encapsulated urea. Thus, not only will a fertilizer such as the urea be released, but also a pesticide.

Urea is a strong hydrogen bonding solvent with a melting point of 140° C. that is incompatible with hydrophobic materials such as the sulfur-alkene copolymer-sulfur-plasticizer system. Since the melting point of urea is so high, some decomposition of thermally sensitive pesticides or destruction of seed tissues might be expected during the coating operation. However, the melting point of urea can be substantially depressed by forming eutectics with the sodium and potassium salts of $SCN^-$, $NO_3^-$ and $HCOO^-$ [G. Vitali, G. Berchiesi and S. Barocci, Thermochemica Acta, 261 (1991)]. Of special interest is the thiocyanate salt which forms a eutectic with urea at 57° C.

In a typical procedure, the hydrophilic pesticide is dissolved in a eutectic of urea and a salt at the eutectic composition and spray quenched to prills which can be subsequently coated with the alkene-sulfur copolymer-sulfur-plasticizer system at temperature below the $T_g$ or the eutectic $T_m$ of the urea salt mixture.

Alternatively, the urea-salt-pesticide melt may be sprayed onto seeds such as corn, soybeans, etc. at temperatures below 60° C. to generate an adherent coating. The alkene-sulfur copolymer-sulfur-plasticizer would then be coated onto the urea system coated seeds held for the minimum at temperatures below 50° C.

Thus, the instant invention provides a solvent-free encapsulating process permitting bacterial attack to release the core material, and in which the by-products, such a sulfur, are environmentally friendly with sulfur essentially becoming sulphuric acid due to the hydrolytic oxidation of the sulfur.

The invention will be further described in connection with the following examples which are set forth for purposes of illustration only.

EXAMPLE 1

A molten eutectic mixture of 68 mole % urea and 32 mole % potassium thiocyanate is extruded through a spray nozzle at 60° C. to produce 100 micron diameter prills. 10 vol. % prills are suspended at 50° C. in a 90 vol. % mixture of 70 wt. % sulfur, 10 wt. % dicyclopentadiene, 10 wt. % dipentene, and 10 wt. % dodecylpolysulfide that had been reacted at 140° C. for 6 hours. This mixture is then extruded into the center of a rapidly rotating disk to produce a fine spray of particles which are rapidly quenched into 25° C. air to produce alkene-sulfur copolymer-sulfur-plasticizer coated urea-salts cores suitable for controlled release of fertilizer.

EXAMPLE 2

A molten eutectic mixture of 68 mole % urea and 32 mole % potassium thiocyanate is extruded through a spray nozzle at 60° C. to coat corn seeds in the fluidized bed state contained within a Wurster air suspension coater. The urea coated seeds are then rapidly separated and cooled to room temperature. Next, the coated seeds are suspended in the Wurster coater and sprayed with a 50° C. mist of 90 vol. % mixture of 70 wt. % sulfur, 10 wt. % dicyclopentadiene, 10 wt. % dipentene, and 10 wt. % dodecylpolysulfide that had been reacted at 140° C. for 6 hours. The alkene-sulfur copolymer-sulfur-plasticizer: urea-salt coated seeds suitable for controlled release of fertilizer are then separated from the coater.

While the invention has been described in connection with a preferred embodiment, it is not intended to limit the scope of the invention to the particular form set forth, but on the contrary, it is intended to cover such alternatives, modifications, and equivalents as may be included within the spirit and scope of the inventions as disclosed and claimed herein.

What is claimed is:

1. A composition comprising a controlled release coated agricultural product comprising an agricultural chemical, seed, or mixture thereof coated with an environmentally degradable amorphous alkene-sulfur copolymer containing dissolved $S_8$ and pollymeric sulfur.

2. The composition of claim 1 containing agricultural products of different thickness coatings.

3. The composition of claim 2 wherein agricultural products have a coating wall thickness of about 2 to 20 microns.

4. The composition of claim 1 wherein the agricultural product is an agricultural chemical that is a fertilizer, soil conditioner, fungicide, insecticide, herbicide, nematocide, plant hormone, insect repellent, or mixture thereof; a seed that is corn, soybean, or sunflower; or a mixture of at least one said agricultural chemical and one said seed.

5. The composition of claim 2 wherein the agricultural product is an agricultural chemical that is a fertilizer, soil conditioner, fungicide, insecticide, herbicide, nematocide, plant hormone, insect repellent, or mixture thereof; a seed that is corn, soybean, or sunflower; or a mixture of at least one said agricultural chemical and one said seed.

6. The composition of claim 3 wherein the agricultural products are an agricultural chemical that is a fertilizer, soil conditioner, fungicide, insecticide, herbicide, nematocide, plant hormone, insect repellent, or mixture thereof; a seed that is corn, soybean, or sunflower; or a mixture of at least one such agricultural chemical and one such seed.

7. The composition of claim 1 wherein said agricultural product is a fertilizer, corn, or a mixture thereof.

8. The composition of claim 2 wherein said agricultural product is a fertilizer, corn, or a mixture thereof.

9. The composition of claim 3 wherein said agricultural product is a fertilizer, corn, or a mixture thereof.

10. A process of making a controlled release coated agricultural product comprising an agricultural chemical, seed, or mixture thereof comprising coating said agricultural product with an environmentally degradable and amorphous alkene-sulfur copolymer containing dissolved $s_8$ and plymeric sulfur, said coating being of a thickness sufficient to control release of said agricultural product due to environmental degradation.

11. The process of claim 10 wherein agricultural products of different thickness are prepared and then admixed.

12. The process of claim 11 wherein said coating has a thickness of about 2 to 20 microns.

13. The process of claim 10 wherein the agricultural product is an agricultural chemical that is a fertilizer, soil conditioner, fungicide, insecticide, herbicide, nematocide, plant hormone, insect repellent, or mixture thereof; a seed that is corn, soybean, or sunflower; or a mixture of at least one said agricultural chemical and one said seed.

14. The process of claim 11 wherein the agricultural product is an agricultural chemical that is a fertilizer, soil conditioner, fungicide, insecticide, herbicide, nematocide, plant hormone, insect repellent, or mixture thereof; a seed that is corn, soybean, or sunflower; or a mixture of at least one said agricultural chemical and one said seed.

15. The process of claim 12 wherein the agricultural product is an agricultural chemical that is a fertilizer, soil conditioner, fungicide, insecticide, herbicide, nematocide, plant hormone, insect repellent, or mixture thereof; a seed that is corn, soybean, or sunflower; or a mixture of at least one said agricultural chemical and one said seed.

16. The process of claim 10 wherein said agricultural product is a fertilizer, corn, or mixture thereof.

17. The process of claim 11 wherein said agricultural product is a fertilizer, corn, or mixture thereof.

18. The process of claim 12 wherein said agricultural product is a fertilizer, corn, or mixture thereof.

19. A process of making a controlled release agricultural product comprising a fertilizer, corn, or mixture of fertilizer and corn comprising coating said agricultural product with a molten environmentally degradable amorphous alkene-sulfur copolymer containing dissolved $S_8$ and ployeric sulfur and cooling said molten copolymer to form a hardened layer thereof about said agricultural product, said coating being of a thickness sufficient to control release of said agricultural product due to microbial degradation.

20. The process of claim 19 wherein said coating has a thickness of about 2 to 20 microns.

* * * * *